(12) United States Patent
Peterson et al.

(10) Patent No.: US 9,119,620 B2
(45) Date of Patent: Sep. 1, 2015

(54) ELASTIC STRIP

(75) Inventors: Donald G. Peterson, Shoreview, MN (US); Cary A. Kipke, Woodbury, MN (US); Daniel T. Popko, Stillwater, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 58 days.

(21) Appl. No.: 13/994,176

(22) PCT Filed: Dec. 22, 2011

(86) PCT No.: PCT/US2011/066817
§ 371 (c)(1),
(2), (4) Date: Jun. 14, 2013

(87) PCT Pub. No.: WO2012/092121
PCT Pub. Date: Jul. 5, 2012

(65) Prior Publication Data
US 2013/0282049 A1 Oct. 24, 2013

Related U.S. Application Data

(60) Provisional application No. 61/427,895, filed on Dec. 29, 2010.

(51) Int. Cl.
| | |
|---|---|
| B32B 9/00 | (2006.01) |
| B32B 33/00 | (2006.01) |
| A61B 17/08 | (2006.01) |
| A61F 5/08 | (2006.01) |
| A61F 13/02 | (2006.01) |

(52) U.S. Cl.
CPC .............. *A61B 17/085* (2013.01); *A61F 5/08* (2013.01); *A61F 13/02* (2013.01); *A61F 13/023* (2013.01); *A61B 2017/086* (2013.01)

(58) Field of Classification Search
CPC ............ A61B 17/085; A61B 2017/086; A61F 13/023; A61F 5/08; A61F 13/02
USPC ................................................. 428/40.1, 41.8
See application file for complete search history.

(56) References Cited

U.S. PATENT DOCUMENTS

| RE24,906 | E | 12/1960 | Ulrich |
|---|---|---|---|
| 3,389,827 | A | 6/1968 | Abere |

(Continued)

FOREIGN PATENT DOCUMENTS

| EP | 941723 | 9/1999 |
|---|---|---|
| EP | 1033118 | 9/2000 |

(Continued)

OTHER PUBLICATIONS

Paris, Stacy. Abstract. Pub. by 43 International Science and Engineering Fair, Nashville, Tennessee, May 10, 1992, p. 257. "STALAR: A More Effective Wound Closure".

(Continued)

*Primary Examiner* — Victor Chang
(74) *Attorney, Agent, or Firm* — 3M Innovative Properties Company

(57) ABSTRACT

The disclosed elastic strip includes an elastic substrate and an overlying carrier. The elastic strip allows for controlled stretch of the elastic substrate. After stretching and applying to skin, the elastic strip can pull portions of the adhered skin. Therefore, the elastic strip can be used as a wound closure or as a nasal dilator, for example.

14 Claims, 3 Drawing Sheets

(56) References Cited

U.S. PATENT DOCUMENTS

| | | | |
|---|---|---|---|
| 3,645,835 | A | 2/1972 | Hodgson |
| 4,112,213 | A | 9/1978 | Waldman |
| 4,310,509 | A | 1/1982 | Berglund |
| 4,323,557 | A | 4/1982 | Rosso |
| 4,472,480 | A | 9/1984 | Olson |
| 4,595,001 | A | 6/1986 | Potter |
| 4,737,410 | A | 4/1988 | Kanter |
| 5,022,389 | A | 6/1991 | Brennan |
| 5,476,091 | A * | 12/1995 | Johnson .................... 128/200.24 |
| 5,669,377 | A | 9/1997 | Fenn |
| 5,769,089 | A | 6/1998 | Hand |
| 5,931,852 | A | 8/1999 | Brennan |
| 6,090,403 | A | 7/2000 | Block |
| 6,196,228 | B1 | 3/2001 | Kreitzer |
| 6,206,902 | B1 | 3/2001 | Morikane |
| 6,276,360 | B1 | 8/2001 | Cronk |
| 6,299,605 | B1 | 10/2001 | Ishida |
| 6,375,667 | B1 | 4/2002 | Ruch |
| 6,386,197 | B1 | 5/2002 | Miller |
| 6,761,896 | B1 | 7/2004 | Znaiden |
| 6,971,388 | B1 | 12/2005 | Michaels |
| 7,414,168 | B2 | 8/2008 | Lebner |
| 2001/0032645 | A1 | 10/2001 | Cronk |
| 2001/0056267 | A1 | 12/2001 | Ishida |
| 2005/0027230 | A1 | 2/2005 | Beaudry |
| 2005/0199245 | A1 | 9/2005 | Brennan |
| 2008/0233348 | A1 | 9/2008 | Ishiwatari |
| 2009/0125052 | A1 * | 5/2009 | Pinna et al. .................... 606/199 |
| 2009/0163844 | A1 | 6/2009 | Gurtner |
| 2012/0221044 | A1 | 8/2012 | Archibald |

FOREIGN PATENT DOCUMENTS

| | | |
|---|---|---|
| NL | 1010444 | 5/2000 |
| WO | WO 97-38651 | 10/1997 |
| WO | WO 98-15242 | 4/1998 |
| WO | WO 99-22678 | 5/1999 |
| WO | WO 99-27880 | 6/1999 |
| WO | WO 99-65430 | 12/1999 |
| WO | WO 01-60294 | 8/2001 |
| WO | WO 01-74432 | 10/2001 |
| WO | WO 02-26181 | 4/2002 |
| WO | WO 03-090791 | 11/2003 |
| WO | WO 2006-099658 | 9/2006 |
| WO | WO 2007-056715 | 5/2007 |
| WO | WO 2010/039771 | 4/2010 |
| WO | WO 2010-056541 | 5/2010 |
| WO | WO 2010-056543 | 5/2010 |

OTHER PUBLICATIONS

International Search Report for PCT International Application No. PCT/US2011/066817, Mailed May 31, 2012, 3 pages.

* cited by examiner

ELASTIC STRIP

CROSS REFERENCE TO RELATED APPLICATIONS

This is a national stage filing under 35 U.S.C. 371 of PCT/US2011/066817, filed Dec. 22, 2011, which claims priority to U.S. Provisional Application No. 61/427,895, filed Dec. 29, 2010, the disclosures of which are incorporated by reference in their entirety herein.

FIELD

The present disclosure relates to an elastic strip. In particular, the present disclosure relates to an elastic strip with a carrier for controlling the overall stretch of the elastic strip.

BACKGROUND

Various types of devices are used on skin to lift portions of the skin or to pull sections of skin together. For example, nasal dilators are applied to the bridge of a nose. The nasal dilator typically includes a mechanical spring and adhesive islands at the ends of the spring that adhere to the skin. Once the adhesive is stuck to the skin, the mechanical spring lifts the skin outward. The mechanical spring adds weight and thickness to the overall nasal dilator. Also, the spring area inhibits the moisture at the skin underlying the spring from passing through the nasal dilator increasing the instances of skin maceration.

Standard wound closures are strips of adhesive tape applied over a wound to prevent the skin surrounding the wound from stretching open. However, standard wound closures are often not elastic and therefore although they can prevent the skin from stretching open, they cannot be placed under tension to secure the wound closed.

SUMMARY

The disclosed elastic strip includes an elastic substrate and an overlying carrier. The elastic strip allows for controlled stretch of the elastic substrate. After stretching and applying to skin, the elastic strip can pull portions of the adhered skin. Therefore, the elastic strip can be used as a wound closure or as a nasal dilator, for example.

In one embodiment, the elastic strip comprises a carrier and an elastic substrate. The carrier has a first carrier end portion and second carrier end portion separated from one another by a carrier midsection. The elastic substrate has a first side comprising an adhesive and second side adjacent the carrier. The elastic substrate has a first substrate end portion, a second substrate end portion, separated from one another by a substrate midsection. The first carrier end portion secures with the first substrate end portion. The second carrier end portion secures with the second substrate end portion. The carrier midsection is disconnected from the substrate midsection.

In one embodiment, the first carrier end portion, second carrier end portion and carrier midsection comprise a continuous sheet of inelastic material. In one embodiment, the carrier sets the maximum stretch of the elastic substrate. In one embodiment, the first carrier end portion is separate from the second carrier end portion. In one embodiment, the first carrier end portion comprises a first inner section at the midsection and the second carrier end portion comprises a second inner section, wherein the first inner section and second inner section overlap one another. In one embodiment, the overlap between the first inner section of the first carrier portion and the second inner section of the second carrier portion provides a control for the stretch of the elastic substrate. In one embodiment, the carrier extends beyond the film to form a tab. In one embodiment, the carrier is removable from the substrate. In one embodiment, the elastic substrate is an elastic nonwoven, woven, knit, or film. In one embodiment, the elastic substrate is a permeable thin film. In one embodiment, the adhesive covers the entire first side of the elastic substrate. In one embodiment, the adhesive on the first side of the elastic substrate is at the first substrate end portion and second substrate end portion, wherein the substrate midsection is free of adhesive. In one embodiment, a release liner covers the adhesive, wherein the release liner is removable from the adhesive. In one embodiment, the adhesive secures to skin.

In one embodiment, the first substrate end portion adheres to skin on a first side of a nose and the second substrate end portion adheres to skin on a second side of the nose, such that the substrate midsection spans the bridge of the nose.

In one embodiment, the first substrate end portion adheres to skin on a first side of a wound and the second substrate end portion adheres to skin on a second side of the wound, such that the substrate midsection spans the wound.

In one embodiment, a method of attaching a strip comprises providing an elastic strip, pulling the first substrate end portion in a first direction, pulling the second substrate end portion in a second direction, opposite the first direction, and adhering the first side to a surface, wherein the elastic substrate retracts. In one embodiment, the method further comprises removing the carrier from the elastic substrate.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention.

The figures may not be drawn to scale.

DETAILED DESCRIPTION

Figure 1:
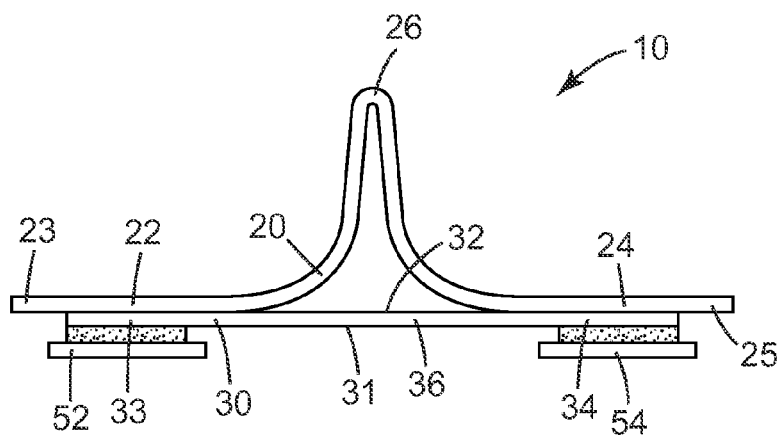
FIG. 1 is a side view of an embodiment of an elastic strip.
Figure 2:
FIG. 2 is a side view of the elastic strip of FIG. 1 stretched.
Figure 3:
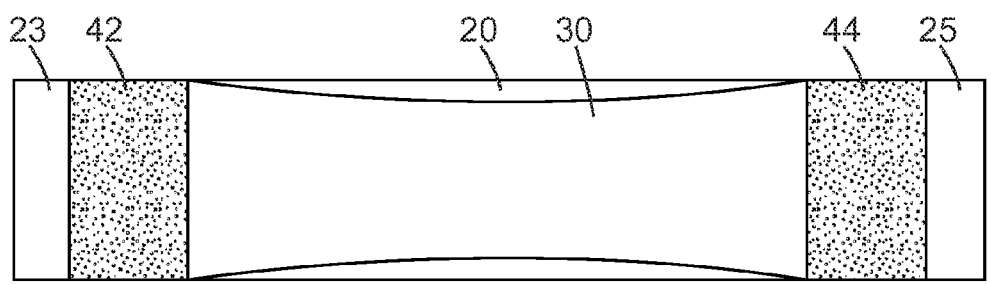
FIG. 3 is a bottom view of the elastic strip of FIG. 2.

FIG. 1 is a side view of an embodiment of an elastic strip 10. FIG. 2 is a side view of the elastic strip 10 of FIG. 1 stretched. FIG. 3 is a bottom view of the elastic strip 10 of FIG. 2.

The elastic strip 10 has a carrier 20 and an elastic substrate 30. In the embodiment shown in FIGS. 1-3, the carrier 20 is a continuous strip and comprises a first carrier end portion 22, a second carrier end portion 24, separated from one another by a carrier midsection 26.

Elastic substrate 30 has a first side 31 and a second side 32. The carrier 20 is at the second side 32. In this embodiment, the elastic substrate 30 is a continuous strip and comprises a first substrate end portion 33, a second substrate end portion 34, separated from one another by a substrate midsection 36.

The carrier 20 attaches to the elastic substrate 30. In one embodiment, the carrier 20 is removably attached to the elastic substrate 30. The first carrier end portion 22 connects with the first substrate end portion 33. The second carrier end portion 24 connects with the second substrate end portion 34. The carrier midsection 36 and the substrate midsection 36 are not connected to one another.

The elastic substrate 30 can stretch and retract. FIG. 1 show the elastic strip 10 with the elastic substrate 30 fully retracted. FIGS. 2 and 3 show the elastic strip 10 fully stretched. Because the carrier 20 secures to the elastic substrate 30, but the carrier midsection 26 and substrate midsection 36 are not secured to one another, the elastic substrate 30 is movable relative to the carrier 20. Therefore, the elastic substrate 30 can stretch when the first substrate end portion 33 is pulled in a direction and the second substrate end portion 34 is pulled in an opposite direction.

The carrier 20 being a continuous substrate secured to the elastic substrate 30 allows for a maximum amount of stretch of the elastic substrate 30. In this embodiment, the maximum stretch is limited by the total overall length of the carrier 20. FIGS. 2 and 3 show the elastic strip 10 in maximum stretch.

FIG. 3 shows the areas of attachment of the elastic substrate 30 to the carrier 20. In this embodiment, the entire adhesive islands 42, 44 represent the areas of securement of the carrier 20 to the elastic substrate. For the embodiment shown in FIG. 1-3, while the elastic strip 10 is stretched, the areas of securement are not stretched and therefore not under tension. Therefore, the adhesive islands can be placed on a surface such as skin without imposing tension or pulling at the adhesive attachment point to the skin. Instead, the adhesive islands 42, 44 secure to the surface and the retraction of the substrate midsection 36 provides pulling.

In one embodiment, the carrier 20 is removable from the elastic substrate 30. To aid in removal, the carrier 20 extends beyond the elastic substrate 30 and forms a first tab 23 and second tab 25. It is understood, that in some embodiments, the carrier 20 may remain fixed to the elastic substrate.

In this embodiment, the first side 31 of the elastic strip 10 has a first adhesive island 42 at the first substrate end portion 33 and a second adhesive island 44 at the second substrate end portion 34. In this embodiment, the substrate midsection 36 does not have an adhesive at the first side 31 of the elastic substrate.

In this embodiment, as shown in FIG. 1, a first release liner 52 is provided over the first adhesive island 42 and a second release liner 54 is provided over the second adhesive island 44. The release liners 52, 54 typically extend beyond the surface of the first or second adhesive island 42, 44 so that a tab is formed to allow for easy removal of the release liner from the adhesive. The release liners 52, 54 are removable from the adhesive islands 42, 44. FIGS. 2 and 3 show the elastic strip 10 with the release liners 52, 54 removed to expose the adhesive 42, 44.

Figure 4:
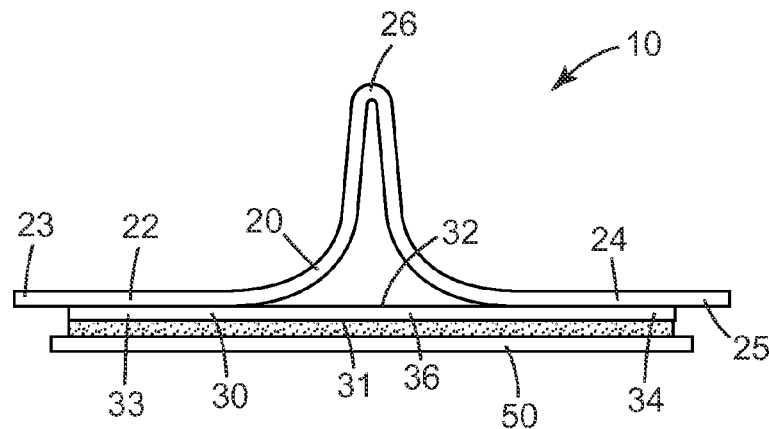
FIG. 4 is a side view of an embodiment of an elastic strip.
Figure 5:
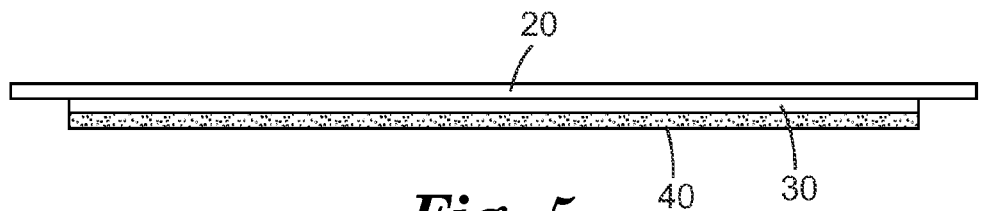
FIG. 5 is a side view of the elastic strip of FIG. 4 stretched.
Figure 6:
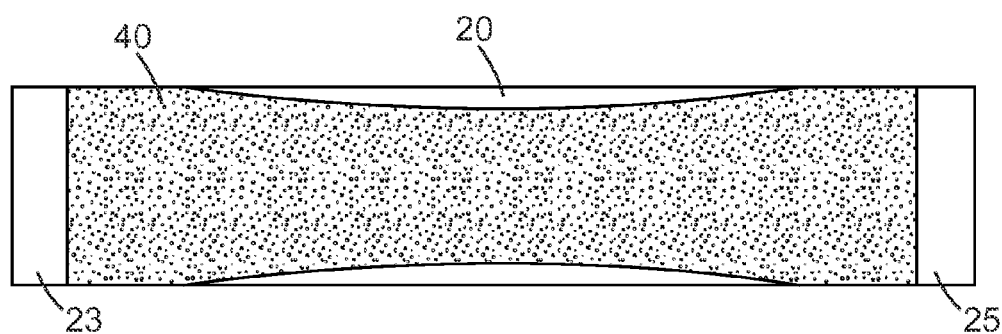
FIG. 6 is a bottom view of the elastic strip of FIG. 5.

FIG. 4 is a side view of another embodiment of an elastic strip 10. FIG. 5 is a side view of the elastic strip 10 of FIG. 4 stretched. FIG. 6 is a bottom view of the elastic strip 10 of FIG. 5.

The elastic strip 10 shown in FIGS. 4-6 includes a carrier 20 and an elastic substrate 30 that is similar to the elastic strip 10 shown in FIGS. 1-3. However, in the embodiment shown in FIGS. 4-6, the first side 31 of the elastic substrate 30 is fully coated with adhesive 40. The embodiment shown in FIGS. 4-6 includes similar areas of securement of the carrier 20 to the elastic substrate 30. The areas of securement are not stretched and therefore not under tension. It is understood that the areas of securement of the carrier 20 to the elastic substrate 30 can include a variety of sizes.

In this embodiment, as shown in FIG. 4, a single release liner 50 is provided over the entire adhesive 40. The release liner 50 extends beyond the surface of the adhesive 40 to allow for easy removal of the release liner 50 from the adhesive 40. The release liner 50 is removable from the adhesive 40. FIGS. 5 and 6 show the elastic strip 10 with the release liner 50 removed.

The carrier 20 can be constructed of a variety of material. The carrier 20 may be a woven, kitted, nonwoven, paper, or film. In one embodiment, the carrier 20 is constructed of a material that has less stretch than the material forming the elastic substrate 30. In one embodiment, the carrier 20 is inelastic and cannot stretch. In one embodiment, the carrier material used is substantially more rigid than the elastic substrate to prevent the elastic substrate from wrinkling during application. Carrier materials can include, but are not limited to, polyethylene/vinyl acetate copolymer-coated papers and polyester films.

Elastic substrate 30 can be constructed of a variety of materials that are able to stretch and retract. The elastic material can have a variety of different amounts of stretch. The elastic material should retract at least 50% of the total stretch distance. In another embodiment, the elastic material retracts at least 75% of the total stretch distance. In another embodiment, the elastic material retracts at least 95% of the total stretch distance.

The elastic substrate 30 may be a woven, knitted, nonwoven, or film. For applications where the elastic strip 10 is applied over skin or wounds, the elastic substrate 30 in combination with the adhesive could have high moisture vapor permeability. One example of a suitable material is a high moisture vapor permeable film such as described in U.S. Pat. Nos. 3,645,835 and 4,595,001, the disclosures of which are herein incorporated by reference. Issued U.S. Pat. Nos. 3,645,835 and 4,595,001, the disclosures of which are hereby incorporated by reference, describe methods of making such films and methods for testing their permeability. Preferably, the film/adhesive composite should transmit moisture vapor at a rate equal to or greater than human skin such as, for example, at a rate of at least 300 g/m$^2$/24 hrs/37° C./100-10% RH, or at least 700 g/m$^2$/24 hrs/37° C./100-10% RH, or at least 2000 g/m$^2$/24 hrs/37° C./100-10% RH using the inverted cup method as described in U.S. Pat. No. 4,595,001. Perforated substrates or films may be used to increase the moisture vapor transmission.

The elastic substrate is preferably conformable to anatomical surfaces. As such, when applied to an anatomical surface, it conforms to the surface even when the surface is moved and can stretch and retract. One embodiment, the elastic substrate is an elastomeric polyurethane, polyester, or polyether block amide films. These films combine the desirable properties of resiliency, high moisture vapor permeability, and transparency.

The adhesive typically is a pressure sensitive adhesive, and particularly adhesives that can be applied to skin such as the acrylate copolymers described in U.S. Pat. No. RE 24,906, the disclosure of which is hereby incorporated by reference, particularly a 97:3 iso-octyl acrylate:acrylamide copolymer. Another adhesive is an 70:15:15 isooctyl acrylate: ethyleneoxide acrylate:acrylic acid terpolymer, as described in U.S. Pat. No. 4,737,410 (Example 31), the disclosure of which is hereby incorporated by reference. Other useful adhesives are described in U.S. Pat. Nos. 3,389,827, 4,112,213, 4,310,509, and 4,323,557, the disclosures of which are hereby incorporated by reference. Inclusion of medicaments or antimicrobial agents in the adhesive is also contemplated, as described in U.S. Pat. Nos. 4,310,509 and 4,323,557 both of which are hereby incorporated by reference.

Silicone adhesive can also be used. Generally, silicone adhesives can provide suitable adhesion to skin while gently removing from skin. Suitable silicone adhesives are disclosed in PCT Publications WO2010/056541 and WO2010/056543, the disclosure of which are herein incorporate by reference.

In one embodiment, the adhesive is able to transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001 and U.S. Pat. App. Pub. 2008-0233348, the disclosure of which are herein incorporated by reference.

Release liners which are suitable for use in the adhesive composites of the present invention can be made of kraft papers, polyethylene, polypropylene, polyester or composites of any of these materials. In one embodiment, the liners are coated with release agents such as fluorochemicals or silicones. For example, U.S. Pat. No. 4,472,480, the disclosure of which is hereby incorporated by reference, describes low surface energy perfluorochemical liners. In one embodiment, the liners are papers, polyolefin films, or polyester films coated with silicone release materials. Examples of commercially available silicone coated release papers are supplied by Wausau Paper Specialty Products (Rhinelander, Wis.) and Mondi Packaging (Lancaster, Ohio). One suitable release liner is a 60# per 3000 square feet bleached kraft SC RLSE D11 442-6001 paper liner available from Wausau Paper Specialty Products.

To make the elastic strip, the carrier 20 is laminated through heat and/or pressure, with or without an additional adhesive layer to the elastic substrate 30 to secure the first carrier end portion 22 to the first substrate end portion 33 and to secure the second carrier end portion 24 to the second substrate end portion 34. In one embodiment, the carrier 20 is heat-sealable to the elastic substrate 30. The adhesive can be applied to the first side 31 of the elastic substrate 30 from known coating techniques.

To use the elastic strip 10, the optional release material is removed from the adhesive. Then, the first carrier end portion 22 is pulled from the second carrier end portion 24, which causes the elastic substrate 30 to stretch, such as shown in FIGS. 2, 3, 5, and 6. The stretched elastic strip 10 is applied to a surface. The user removes the force applying the stretch and the elastic strip 10 retracts. Optionally, the carrier 20 can be removed from the elastic strip 10 once the elastic strip is applied.

Figure 7:
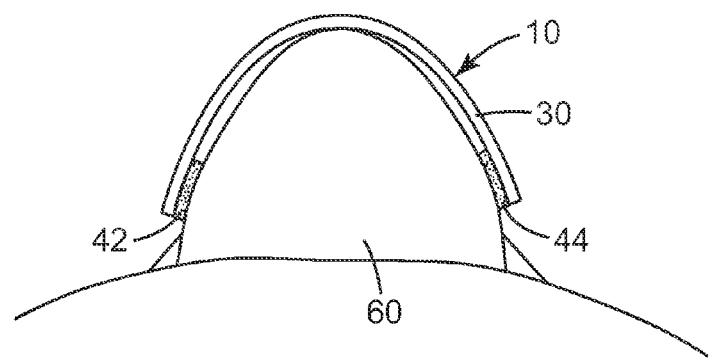
FIG. 7 is a top view of an embodiment of an elastic strip applied to a nose.

FIG. 7 is a top view of an embodiment of an elastic strip 10 as described in the embodiment shown in FIG. 1-3, applied to a nose 60 for use as a nasal dilator. The elastic strip 10 is applied to the nose 60 while stretched. Then, the force applying the stretch is removed and the elastic strip 10 retracts. During retraction, the elastic strip 10 provides a pulling force to the skin of the nose 60 and therefore functions as a nasal dilator. In this embodiment, the carrier 20 has been removed.

Figure 8:
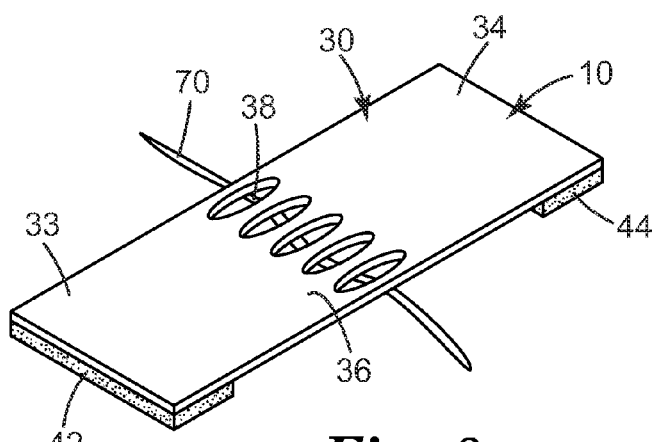
FIG. 8 is a perspective view of an embodiment of an elastic strip applied over a wound.

FIG. 8 is a perspective view of an embodiment of an elastic strip 10 applied over a wound 70. The elastic strip 10 is applied over a wound 70 while stretched such that the first substrate end portion 33 is on one side of the wound 70 and the second substrate end portion 34 is on an opposite side of the wound 70. Then, the force applying the stretch is removed and the elastic strip 10 retracts. During retraction, the elastic strip provides a pulling force to the skin to hold the wound 70 closed. As shown in this embodiment, it may be desirable to include openings 38 in the elastic substrate 30 at the substrate midsection 36 to allow for wound fluid to pass through. These openings 38 can also be used to modify the closure or pull force for different elastic materials. It is understood that an overlying absorbent dressing may be applied to the wound 70. Also, in this embodiment, the overlying carrier 20 has been removed.

Figure 9:
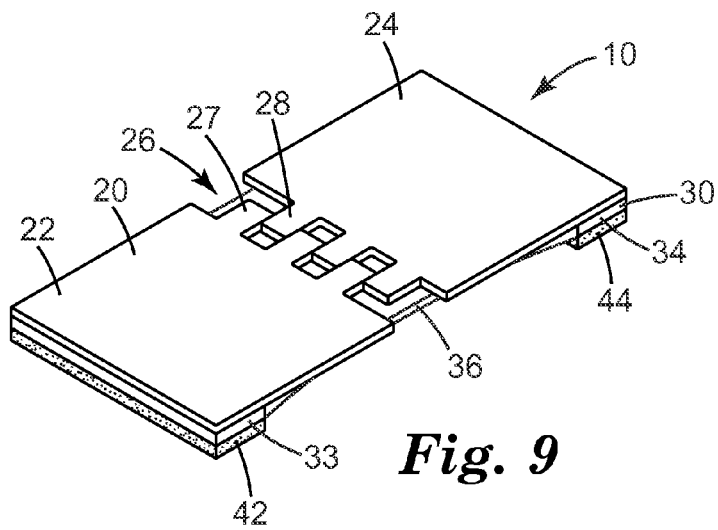
FIG. 9 is a perspective view of an embodiment of an elastic strip.

FIG. 9 is a perspective view of an embodiment of an elastic strip 10. The elastic strip 10 is similar to the elastic strip 10 shown in FIGS. 1-6 by having a carrier 20 and an elastic substrate 30 connected to one another in a similar way as described in FIGS. 1-6. As described above, the elastic substrate 30 can stretch and retract. The carrier 20 secures to the elastic substrate 30, but the carrier midsection 26 and substrate midsection 36 are not secured to one another. Therefore, the elastic substrate 30 is movable relative to the carrier 20 and can stretch when the first substrate end portion 33 is pulled in a direction and the second substrate end portion 34 is pulled in an opposite direction. In this embodiment, the adhesive includes a first adhesive island 42 and second adhesive island 44 similar to the embodiment shown in FIGS. 1-3. However, in the embodiment shown in FIG. 9, the carrier 20 is a discontinuous strip, wherein the first carrier end portion 22 is separated from the second carrier end portion 24 at the carrier mid section 26.

The first carrier end portion 22 at the carrier midsection 26 has a first inner section 27. The second carrier end portion 24 at the carrier midsection 26 has a second inner section 28. The first inner section 27 and second inner section 28 include interengaging or overlapping sections that move closer to one another when the elastic strip 10 is in a retracted position and move away from one another when the elastic strip 10 is in a stretched position, as shown in FIG. 9. Therefore, through visual identification, a user can control the level of stretch of the elastic strip 10. The first and second inner sections 27, 28 can include indicia for indicating the predetermined appropriate level of stretch for a particular application. It is understood, that with this embodiment, various levels of stretch could be controlled. It is understood that the carrier 20 disclosed in FIG. 9 could be utilized in various configuration and applications. It is understood that the materials shown and described above could be utilized for the embodiment shown and described in this embodiment depicted in FIG. 9.

It is understood that the elastic strip could be any size or shape suitable for a particular application and that the elastic strip is not limited to a rectangular shape. Also, several elastic strips could be used together depending on the application.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

What is claimed is:

1. An elastic strip comprising:
a carrier having a first carrier end portion and second carrier end portion separated from one another by a carrier midsection;
an elastic substrate which is a continuous strip with a first side comprising an adhesive and second side adjacent the carrier, wherein the elastic substrate has a first substrate end portion, a second substrate end portion, separated from one another by a substrate midsection;
wherein the first carrier end portion secures with the first substrate end portion, the second carrier end portion secures with the second substrate end portion, and the carrier midsection is disconnected from the substrate midsection.

2. The elastic strip of claim 1, wherein the first carrier end portion, second carrier end portion and carrier midsection comprise a continuous sheet of inelastic material.

3. The elastic strip of claim 2, wherein the carrier sets the maximum stretch of the elastic substrate.

4. The elastic strip of claim 1, wherein the first carrier end portion is separate from the second carrier end portion.

5. The elastic strip of claim 4, wherein the first carrier end portion comprises a first inner section at the midsection and the second carrier end portion comprises a second inner section, wherein the first inner section and second inner section overlap one another.

6. The elastic substrate of claim 5, wherein the overlap between the first inner section of the first carrier portion and the second inner section of the second carrier portion provides a control for the stretch of the elastic substrate.

7. The elastic strip of claim 1, wherein the carrier extends beyond the elastic substrate to form a tab.

8. The elastic strip of claim 1, wherein the carrier is removable from the elastic substrate.

9. The elastic strip of claim 1, wherein the midsection of the elastic substrate includes openings.

10. The elastic strip of claim 1, wherein the adhesive covers the entire first side of the elastic substrate.

11. The elastic strip of claim 1, wherein the adhesive on the first side of the elastic substrate is at the first substrate end portion and second substrate end portion, wherein the substrate midsection is free of adhesive.

12. The elastic strip of claim 1, wherein the first substrate end portion adheres to skin on a first side of a nose and the second substrate end portion adheres to skin on a second side of the nose, such that the substrate midsection spans the bridge of the nose.

13. The elastic strip of claim 1, wherein the first substrate end portion adheres to skin on a first side of a wound and the second substrate end portion adheres to skin on a second side of the wound, such that the substrate midsection spans the wound.

14. A method of attaching a strip comprising the steps of:
providing the elastic strip of claim 1;
pulling the first substrate end portion in a first direction;
pulling the second substrate end portion in a second direction, opposite the first direction;
adhering the first side to a surface;
wherein the elastic substrate retracts.

* * * * *